United States Patent
Hilscher et al.

(10) Patent No.: US 9,857,297 B2
(45) Date of Patent: Jan. 2, 2018

(54) METHOD FOR CLASSIFYING SEEDS

(71) Applicant: KWS SAAT SE, Einbeck (DE)

(72) Inventors: Elke Hilscher, Einbeck (DE); Frank Friedhoff, Einbeck (DE); Christian Hirschmann, Kalefeld (DE)

(73) Assignee: KWS SAAT SE, Einbeck (DE)

( * ) Notice: Subject to any disclaimer, the term of this patent is extended or adjusted under 35 U.S.C. 154(b) by 0 days.

(21) Appl. No.: 15/107,982

(22) PCT Filed: Dec. 23, 2014

(86) PCT No.: PCT/DE2014/000644
§ 371 (c)(1),
(2) Date: Jun. 24, 2016

(87) PCT Pub. No.: WO2015/096827
PCT Pub. Date: Jul. 2, 2015

(65) Prior Publication Data
US 2016/0327478 A1    Nov. 10, 2016

(30) Foreign Application Priority Data

Dec. 24, 2013   (DE) .................. 10 2013 021 898

(51) Int. Cl.
*B07C 5/342* (2006.01)
*G01N 21/3586* (2014.01)
(Continued)

(52) U.S. Cl.
CPC ....... *G01N 21/3586* (2013.01); *B07C 5/3416* (2013.01); *B07C 5/3425* (2013.01);
(Continued)

(58) Field of Classification Search
CPC .......... G01N 21/3586; G01N 21/3563; G01N 2201/0697; G01N 2201/06113; B07C 5/3416; B07C 5/342; B07C 5/3425
See application file for complete search history.

(56) References Cited

U.S. PATENT DOCUMENTS 6,706,989 B2 * 3/2004 Hunter .................. A01C 1/00
                                                         209/576
2004/0055211 A1   3/2004 Lestander et al.
(Continued)

FOREIGN PATENT DOCUMENTS

EP    1188041 B1    8/2003
EP    2140749 A1    1/2010
(Continued)

OTHER PUBLICATIONS

Dorney, Timothy D. et al., "Material parameter estimation with terahertz time-domain spectroscopy", J. Opt. Soc. Am, A. (2001), vol. 18, No. 7, pp. 1562-1571.
(Continued)

*Primary Examiner* — Mark Beauchaine
(74) *Attorney, Agent, or Firm* — Troutman Sanders LLP

(57) ABSTRACT

The present invention relates to a method for classification and/or sorting of seeds with the help of terahertz time-domain spectroscopy, use of terahertz time-domain spectroscopy for classification and/or sorting of seeds and seeds classified and/or sorted with terahertz time-domain spectroscopy.

16 Claims, 20 Drawing Sheets

Figure 1:
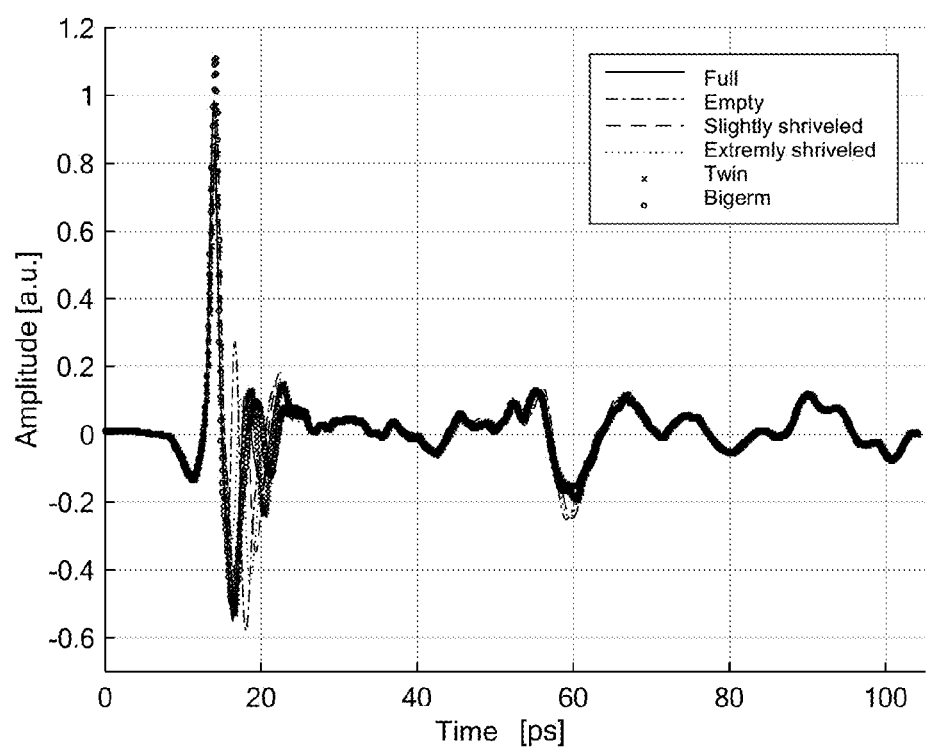

(51) Int. Cl.
 G01N 21/3563 (2014.01)
 G01N 33/00 (2006.01)
 B07C 5/34 (2006.01)

(52) U.S. Cl.
 CPC ..... *G01N 21/3563* (2013.01); *G01N 33/0098* (2013.01); *G01N 2201/0697* (2013.01); *G01N 2201/06113* (2013.01)

(56) References Cited

U.S. PATENT DOCUMENTS

| | | | |
|---|---|---|---|
| 2004/0267457 A1 | 12/2004 | Timmis et al. | |
| 2008/0015790 A1 | 1/2008 | Timmis et al. | |
| 2009/0059205 A1* | 3/2009 | Itsuji | G01N 21/3581 356/51 |
| 2009/0075325 A1 | 3/2009 | Das et al. | |
| 2013/0126399 A1* | 5/2013 | Wolff | B07C 5/3425 209/555 |
| 2013/0229647 A1 | 9/2013 | Fredlund et al. | |

FOREIGN PATENT DOCUMENTS

| | | |
|---|---|---|
| JP | 2009042207 A | 2/2009 |
| WO | 2010000266 A1 | 1/2010 |
| WO | 2012001133 A2 | 1/2012 |

OTHER PUBLICATIONS

Duvillaret, Lionel et al., "A Reliable Method for Extraction of Material Parameters in Terahertz Time-Domain Spectroscopy", IEEE Journal of Selected Topics in Quantum Electronics (1996), vol. 2, No. 3, pp. 739-746.

Genie, R. et al., "Determination of leaf water content from terahertz time-domain spectroscopic data", Journal of Infrared, Millimeter, and Terahertz Waves (2013), pp. 1-8.

Guo, Tiantian et al., "Evalution of wheat seeds by terahertz imaging", 6th UK, Europe, China Millimeter Waves and Thz Technology Workshop (UCMMT), IEEE (2013), 2 pages.

International Search Report and Written Opinion Issued in International Application No. PCT/DE2014/000644 dated Apr. 17, 2015 and English Translation Thereof, 19 pages.

Jördens, C. et al., "Evaluation of leaf water status by means of permittivity at terahertz frequencies", J. Biol. Phys. (2009), vol. 35, pp. 255-264.

Koch, M. et al., "THz-imaging: a new method for density mapping of wood", Wood Science and Technology (1998), vol. 32, pp. 421-427.

Jiang, Ling et al., "Study of DNA Fingerprint of Pine Wood Nematode Based on Terahertz Spectroscopic Technology at 0-10 THz", PIERS Proceedings, Taipei (2013), pp. 430-433.

Maisl, Michael et al., "Automatic CT System with Integrated Evaluation", Annual DACH Conference in Graz (2012) and Supplemental Figures, English Translation Thereof, 15 pages total.

Palka, N. et al., "Terahertz Spectra of Explosives Measured by Optical Parametric Oscillator-Based System and Time Domain Spectroscopy", Acta Physica Polonica A (2012), vol. 122, No. 5, pp. 946-949.

Sun, Jinhai et al., "Identifying Type of Maize with Terahertz Time-domain Spectroscopy", Third International Conference on Biomedical Engineering and Informatics (BMEI 2010), pp. 918-921.

* cited by examiner

METHOD FOR CLASSIFYING SEEDS

CROSS-REFERENCE TO RELATED APPLICATIONS

This application is a U.S. National Stage of International Patent Application No. PCT/DE2014/000644 filed Dec. 23, 2014, which claims the benefit of German Patent Application No. DE 102013021898.5 filed Dec. 24, 2013, both of which applications are herein incorporated by reference in their entireties.

The present invention relates to methods for classifying seed and for sorting seed. The invention relates in particular to methods for classifying and/or sorting seed by using radiation in the terahertz range, for example, by means of terahertz time-domain spectroscopy.

In agriculture, farmers have always needed high-quality seeds. High-quality seeds are characterized by a high germination ability, a high driving force and a homogeneous emergence behavior, among other things. To be able to supply high-quality seeds, seed producers must classify and sort their seeds in order to be able to differentiate and separate high-quality seeds from lower quality seeds. Easily determined physical differences in phenotype, for example, size differences and/or weight differences between seed grains containing an embryo and seed grains containing no embryo, are generally used for this classification and/or sorting.

To supply the highest quality seed, however, a finer differentiation of the seed is necessary. For example, the seeds of sugar beets (*Beta vulgaris*) can be divided into six different classes:
class 1—empty grains (no embryo)
class 2—full grains (with a fully developed embryo)
class 3—slightly shrunken or shriveled (with a slightly shrunken embryo)
class 4—severely shrunken or shriveled (with a severely shrunken embryo)
class 5—twin (with 2 embryos in one seed coat)
class 6—bigerms (with 2 embryos in two seed coats)

In sorting seeds, the goal is to obtain if possible only grains with a fully developed embryo in the "good seed" classification. With respect to the aforementioned example of the sugar beet seed, this means that both grains of class 1 and grains of classes 3 to 6 should be sorted out. Furthermore it is important to ensure that the amount of grains of class 2 falsely sorted out as "bad seed" is preferably not too great.

Because seed grains differ greatly in their properties, the aforementioned goal is achieved only when the selection limits for sorting the seeds are adjusted into individual classes very narrowly and with a low tolerance. To adjust the selection limits, samples are taken regularly for checking on the quality of preparation and are sent for X-ray diagnostic testing with manual evaluation of the image. Automation or personnel-independent evaluation of this quality control has not yet been possible. Furthermore, the ionizing radiation which is used in quality control by X-ray diagnostics and is hazardous to health requires extensive safety measures for the personnel. Furthermore, the possibility of harmful effects of the ionizing X-ray radiation on the seeds also cannot be ruled out. Therefore, X-ray diagnostics are not even used in preparation and sorting of seeds, but instead X-ray diagnostics are used only for testing the quality of the sampling of the seeds that have been sorted into classes accordingly.

Computer tomography is known to be an alternative to quality control of seeds by means of X-ray diagnostics (M. Maisl et al., "Automatic CT System with Integrated Analysis," DACH Annual Convention 2012 in Graz—Mi.1.B.1, pages 1-7). However, the CT system proposed there with an automatic sample changer and automatic image processing is highly complex and can be automated only to a limited extent, so that this method is also used only in process control for verifying the preparation quality as part of sugar beet seed production, but not in seed processing itself.

Other methods such as pulse thermography, a known non-destructive test method, are superior in informational relevance to traditional techniques such as X-ray, ultrasound and eddy current, but they have not been successful in the sorting and classification of seeds.

In addition, US 2013/0229647 A1 discloses a method for classifying seeds, in particular sugar beet seeds, which allows classification of the seeds on the basis of differences in the development of the embryo contained in the seed, based on information from recorded spectra in the IR frequency range. However, the informational relevance of the IR spectra is limited, so that a reliable assignment of a seed to a defined class is often impossible.

The object was therefore to provide a method that would permit automatic classification and/or sorting of seeds on the basis of the various parameters that define the classes of the respective seed and could preferably be used themselves, not only in process control but also in seed processing in order to achieve a higher sorting precision with a higher yield there.

This object is achieved by a method for classifying and/or sorting seed using radiation in the terahertz range, for example, by means of terahertz time-domain spectroscopy.

Terahertz time-domain spectroscopy (THz-TDS) uses terahertz radiation to investigate samples. This technique is suitable for quantitative and qualitative determination of parameters of a wide variety of materials (L. Duvillaret, F. Garet & J. L. Coutaz (1996)): A reliable method for extraction of material parameters in terahertz time-domain spectroscopy. *Selected Topics in Quantum Electronics, IEEE Journal of* 2(3), 739-746; T. D. Dorney, R. G. Baraniuk & D. M. Mittleman (2001): Material parameter estimation with terahertz time-domain spectroscopy. *JOSA A*, 18(7), 1562-1571). Terahertz radiation is electromagnetic radiation in the electromagnetic spectrum between infrared radiation and microwave radiation. Terahertz radiation consists of electromagnetic waves with frequencies between 100 gigahertz (GHz) and 10 terahertz (THz).

In terahertz time-domain spectroscopy, a sample to be examined is exposed to a very short pulse of electromagnetic radiation with a frequency in the terahertz range. To do so, a very short pulse of terahertz radiation is created with a very short pulsed laser because in semiconductors or nonlinear optical materials, ultra-short laser pulses with a duration of a few femtoseconds (1 fs=$10^{-15}$ s) can generate terahertz pulses in the picosecond range (1 ps=$10^{-12}$ s) consisting of only one or two cycles of electromagnetic oscillation. They can also be measured coherently, i.e., with time resolution by using electro-optical methods.

In terahertz time-domain spectroscopy, the THz pulse is divided into two parts, one of which is used to for generation and the other for detection. The THz pulse can be scanned due to the relative time lag. The electrical field of a THz pulse is detected by means of coherent detection, i.e., the THz wave is detected in amplitude and phase. Broad-band spectral information about the sample to be examined can be made with the help of a Fourier analysis of the recorded THz signals and this information then allows inferences regarding parameters of the material.

The signal of the THz pulse thus generated may contain frequency components with which the entire terahertz range can be covered and is usually measured after being reflected on a sample or after being transmitted through the sample and compared with the input pulse as a reference. For analysis of the signal, the signal amplitudes, the time delay, the phase and/or spectrum can be utilized. The change in amplitude, for example, provides information about the properties of the sample, such as its porosity, absorption, thickness and homogeneity. The delay in the THz pulse in its passage through the sample may be due to the optical thickness of the sample (refractive index n times the geometric thickness d). Additional echo pulses which are more or less superimposed, depending on the sample thickness, may occur due to multiple reflections within the sample. The field oscillations following the main pulse contain the spectral information of the sample, which is accessible through a Fourier transformation of the waveform over time.

It is known that terahertz radiation can be used to determine the water content of plants, in particular the water content of leaves (Jördens et al.: J. Biol. Phys. 35: 255-264 (2009); Gente et al.: J. Infrared Milli Terahertz Waves 34: 316-323 (2013); JP 2009/042207 A). Furthermore, with the help of terahertz spectroscopy the density of wood can be determined (Koch et al.: Wood Sc. and Techn. 32: 421-427 (1998)) or the infestation of wood with nematodes (Liang et al.: PIERS Proceedings, Taipei, Mar. 25-28, 2013: 430-433).

The present invention is based on the use of terahertz time-domain spectroscopy to characterize seeds. The characterization relates to parameters, which allow the seeds to be assigned to different quality classes. Such parameters include in particular morphological structures of seeds, such as the presence of certain structural elements in the interior of the seed grain (e.g., the presence of an embryo) or the arrangement of structural elements in the interior of the seed (e.g., two embryos in one seed coat or in two seed coats).

In a first aspect of the present invention, a method for classification and/or sorting of seeds is made available, wherein seeds are classified and/or sorted using radiation in the terahertz range, for example, by means of terahertz time-domain spectroscopy.

A second aspect of the invention is the use of terahertz time-domain spectroscopy for classification and/or sorting of seeds.

A third aspect of the invention relates to seeds that have been classified and/or sorted by means of terahertz time-domain spectroscopy.

The method for classification and/or sorting of seeds according to the first aspect of the invention may include the following steps:
  applying a terahertz pulse to the seed grain,
  measuring the signal generated by the terahertz pulse after transmission and/or reflection by the seed grain,
  determining the amplitude, time lag, phase and/or spectrum of the signal due to the transmission and/or reflection, and
  assigning the seed grain to a predetermined seed class.

In addition, the method for classifying and/or sorting seeds according to the first aspect of the invention may also include an upstream step of introducing a seed grain into the measurement range of a terahertz time-domain spectrometer and/or a downstream step of removing the seed grain from the measurement range of the terahertz time-domain spectrometer.

In one embodiment of the method, the seed grain is assigned to a predetermined seed class on the basis of a calibration of the terahertz time-domain spectroscopy on the basis of reference values and/or reference grains for at least one of the seed classes, preferably for the desired seed class, i.e., the seed class with the high-quality seed. In another embodiment, calibration of the terahertz time-domain spectroscopy is performed on the basis of reference values and/or reference grains for each of the seed classes provided.

By classification of a plurality of seed grains of a sample, the quality of the sample can be determined by ascertaining how large the amount of seed grains of each seed class in the sample is. The classification of the individual seed grains is made on the basis of a plurality of seed grains in a terahertz time-domain spectrometer one after the other.

In an additional and/or alternative embodiment, the seed grain is sorted according to its classification after being removed from the measurement range of the terahertz spectrometer. This embodiment makes it possible to sort out the seed grains that do not belong in the desired seed class. It is thus possible to also improve the quality of the seed with this method because only the seed grains of the desired class can be used for further seed processing or production. Seed grains that do not belong in the desired seed class can be sorted out before further processing of the seeds.

According to the first aspect of the invention, the method for classification and/or sorting of seeds has a sorting accuracy of preferably at least 75%, 76%, 77%, 78%, 79% or 80%, especially preferably at least 81%, 82%, 83%, 84%, 85%, 86%, 87%, 88%, 89% or 90% and most especially preferably at least 90%, 91%, 92%, 93%, 94%, 95%, 96%, 97%, 97.5%, 98%, 98.5%, 99%, 99.5% or 100%.

In an additional or alternative embodiment of the method, the seed to be classified and/or sorted with the help of the terahertz time-domain spectroscopy for example, according to the size of the seed grains. It is possible in this way to supply only seed grains of the same or approximately same caliber to the method for classification and/or sorting of seeds. In this embodiment, the seeds are thus calibrated before being classified. This embodiment can further increase the accuracy of the seed classification and/or sorting as needed.

In one embodiment of the method according to the first aspect of the invention, the THz radiation of the THz pulse has a frequency of at least 0.1 THz, preferably at least 0.5 THz, especially preferably at least 1 THz and most especially preferably at least 5 THz.

In an alternative and/or additional embodiment, the THz radiation of the THz pulse has a frequency of no more than 10 THz, preferably no more than 6 THz, especially preferably no more than 4 THz and most especially preferably no more than 3 THz.

In an additional and/or alternative embodiment, the terahertz pulse has a duration in the range of approx. 3 ps to approx. 25 ps, preferably approx. 5 ps to approx. 20 ps and especially approx. 15 ps. In particular, this is preferably a femtosecond laser, which is linearly polarized, emits at 1560 nm or operates at an average laser output power of >60 mW with a repeat frequency of 100 MHz. A pulse length of <90 fs after 2.5 meters of fiber optics is especially preferred. In an additional or alternative embodiment, the terahertz spectrometer has one or more of the following components: a laser source, preferably with fiber optics, a delay zone with a scanning range of preferably 0-300 ps, a terahertz emitter antenna and a terahertz receiver antenna, optics compatible with terahertz, a lock-in amplifier and/or a computer unit with a measurement program for data acquisition and analysis. The spectrometer especially preferably offers a dynamic range of >70 dB and a spectral range of >3.5 THz.

In a particularly preferred embodiment, a terahertz measurement is performed with the following settings: a spectral measurement range of 0.01-10 THz and a delay of 0-104 ps with an interval of 0.05 ps. The integration time per delay setting is 30 ms, which yields a total measurement time of approx. 1 minute per seed grain.

Since terahertz time-domain spectroscopy is a non-contact non-destructive method, any seed can be classified and/or sorted in principle with the help of this method.

In one embodiment of the method according to the first aspect of the invention, the seed is selected from the group of fruits in which the pericarp or a portion of the pericarp, i.e., the endocarp, the mesocarp and/or the exocarp, is lifnified.

In an additional or alternative embodiment, the seeds are selected from the group comprising vegetable seeds, cereal seeds, grains of stone fruits, grains of berries, nuts and grains of fox's bush (amaranth).

In an additional or alternative embodiment, the vegetable seeds are selected from a group comprising seeds of lettuce, seeds of cruciferous vegetables (*brassica*), seeds of blooming vegetables, fruit vegetables, tuberous vegetables, bulb vegetables, legumes and other vegetables. The lettuces include:

Garden lettuce (*Lactuca sativa* L.), for example, head lettuce (*Lactuca sativa* L. var. *capitata* L.), leaf lettuce (*Lactuca sativa* L. var. *crispa* L.), romaine lettuce (*Lactuca sativa* L. var. *longifolia* L.), *asparagus* lettuce (*Lactuca sativa* var. *angustana*) and iceberg lettuce, Common chicory (*Cichorium intybus* L.), for example, head chicory (*Cichorium intybus* var. *foliosum*) and endive (*Cichorium endivia* L.), Rucola, arugula (*Diplotaxis tenuifolia* or *Eruca sativa*), chard (*Beta vulgaris* subsp. *vulgaris*), spinach (*Spinacia oleracea* L.), Chinese spinach (*Ipomoea aquatica* FORSSK.), orache spinach (*Atriplex hortensis* L.), watercress (*Nasturtium officinale* R.BR.), portulaca (*Portulaca* ssp. *sative* (HAW) ČEL.), winter purslane (=Cuban spinach, winter *portulaca*, miner's lettuce *Claytonia perfoliata* DONN. EX WILLD), Malabar spinach, Indian spinach (*Basella alba*), Newzealand spinach, Newzealand spinach (*Tetragonia tetragonioides*), toothache plant (Jambú, *Acmella oleracea* (L.) R. K. JANSEN), jute leaves (*Corchorus olitorius* L.), ice plant (*Mesembryanthemum crystallinum*), daylilies, e.g., the yellow-red daylily (*Hemerocallis fulva* L.), running strawberry blite (*Chenopodium capitatum* (L.) ASCH), Good King Henry herb (*Chenopodium bonus-henricus* L.), and garden dock (*Rumex*).

Crucifer refers to vegetables of the *Brassica* type, including Mediterranean cabbage (*B. fruticulosa*), red cabbage, also called Indian mustard or Serepta mustard (*B. juncea*), rapeseed and rutabaga (*B. napus*), for example rutabaga, Swedish turnip, rapeseed (*B. napus* subsp. *rapifera* MTZG.), turnip (*B. napus* subsp. *napus* L.) and rape kale (*B. napus* subsp. *pabularia*), black mustard (*B. nigra* (L.) KOCH), kohlrabi (*B. oleracea* L.), for example, cauliflower (*B. oleracea* var. *botrytis* L.) such as Romanesque cauliflower (*B. oleracea* convar. *botrytis* var. *botrytis* L.), broccoli (*B. oleracea* var. *Italica* Plenck), kohlrabi (*B. oleracea* var. *gongylodes* L.), head cabbage (*B. oleracea* convar. *capitata* L.), red cabbage (*Brassica oleracea* convar. *capitata* var. *rubra* L.), white cabbage (*Brassica oleracea* convar. *capitata* var. *alba* L.) such as pointed cabbage and savoy cabbage (*B. oleracea* convar. *capitata* var. *sabauda* L.), Brussels sprouts (*B. oleracea* var. *gemmifera* DC.); curly kale (*B. oleracea* var. *sabellica* L.); palm kale (*Brassica oleracea* var. *palmifolia* DC.); marrow-stem kale (*B. oleracea* var. *medullosa* Thell.); *Brassica* (*B. rapa* L.) such as canola (*B. rapa* subsp. *oleifera*); (*B. rapa* subsp. *pekinensis*); pak Choi (*B. rapa* subsp. *chinensis*) and May turnip, autumn turnip, white turnip, Teltow turnip, Bavarian turnip (*B. rapa* subsp. *rapa*), for example, rapini.

The fruit vegetables include artichoke (*Cynara scolymus*), zucchini (*Curcubita pepo* subsp. *pepo* convar. *giromontiina*), cauliflower (*Brassica oleracea* var. *botrytis* L.), broccoli (*Brassica oleracea* var. *Italica* Plenck), Romanesque cauliflower (*Brassica oleracea* convar. *botrytis* var. *botrytis*), lilies (*Lilium* L.) (lily family) and dahlias (*Dahlia* CAV.).

Fruit vegetables are to be understood as the following in the sense of the invention:

Watermelon (*Citrullus lanatus* (THUNB.) MATSUM & NAKAI.),

Cucumber (*Cucumis* L.), for example, honeydew melon (*Cucumis melo* L.), kiwano (*Cucumis metuliferus* E. MEY. EX NAUDIN) and cucumber (*Cucumis sativus* L.), Pumpkins, squashes and zucchini (*Cucurbita*), for example, vegetable marrow, zucchini, spaghetti squash (*C. pepo* L.), winter squash or vegetable marrow (*C. maxima*), field pumpkin (*C. moschata*) and figleaf gourd or Asian pumpkin (*C. ficifolia*), Bitter melon (*Momordica* L.), calabashes (*Lagenaria siceraria* (MOLINA) STANDL.), loofah (*Luffa* MILL), *sechium*, for example, chayote=christophine, (*Sechium edule* (JACQ.) SW), tomato (*Solanum lycopersicum* L.), peppers (*Capsicum* L.), amaranth (*Amaranthus* L.), eggplant (*Solanum melongena*), avocado (*Persea americana* MILL), okra (*Abelmoschus esculentus* (L.) MOENCH), and bread-fruit (*Artocarpus altitis* (PARKINS. EX DU ROI) FOSB. CORR. ST. JOHN).

The root vegetables include tubers and bulb vegetables. The tubers include carrot, purple carrot (*Daucus carota* L. ssp. *sativus*), beet root, red beet (*Beta vulgaris* subsp. *vulgaris*), rutabaga, rutabaga (*Brassica napus* subsp. *rapifera*), May turnip (*Brassica rapa* subsp. *rapa* var. *majalis*) and Teltow turnip (*Brassica rapa* subsp. *rapa* var. *pygmaea*), horseradish (*Armoracia rusticana* GAERTN. MEY. & SCHERB.), radish (*Raphanus sativus* L. subsp. *sativus*), daikon radish (*Raphanus sativus* var. *longipinnatus*), black winter radish (*Raphanus sativus* subsp. *niger* var. *niger*), wasabi (*Wasabia japonica* MATSUM.), potato (*Solanum tuberosum* L.), black salsify (*Scorzonera hispanica* L.), parsnip (*Pastinaca sativa*), bulbous oatgrass (*Petroselinum crispum* subsp. *tuberosum*), celery (*Apium graveolens*), turnip-root chervil or bulbous chervil (*Chaerophyllum bulbosum* L.), lotus pod (*Nelumbo*) and Chinese yam (*Dioscorea.* L.').

Bulb vegetables include the leek family (*Allium*), for example, *Allium* leek onion (*A. cepa* L.), scallion, spring onion (*A. fistulosum* L.), garlic (*A. sativum* L.), shalot (*A. ascalonicum* STRAND.), leeks (*A. porrum* L.), pearl onion (*Allium porrum* var. *sectivum*) and wild garlic (*Allium ursinum*).

The legumes include:
*Phaseolus*
  Lima bean (*Phaseolus lunatus* L.), lima bean
  Tepary bean (*Phaseolus acutifolius* A. GRAY)
  Scarlet runner (*Phaseolus coccineus* L.), haricot bean
  Common bean, bush bean, pole bean (*Phaseolus vulgaris* L.)

Varieties:
    Kidney beans
    Peaberry
    Pinto beans
    Black beans, Brazilian beans
    White beans
Soybean (*Glycine max* (L.) Merill)
Peas (*Pisum*)
    Shelling peas (*Pisum sativum* L. convar. *sativum*), also known as Pahls beans
    Marrow peas (*Pisum sativum* L. convar. *medullare* Alef. emend. C. O. Lehm)
    Sugar peas (*Pisum sativum* L. convar. *auphium* Alef emend. C. O. Lehm), also known as snow peas or (sugar) snap peas
    Giant pea pod (*Pisum granda sneida* L. convar. *sneidulo* p. *shneiderium*)
Cut-leaved medick (*Medicago* L.)
    Common alfalfa, alfalfa (*M. sativa* L.)
Chickpea (*Cicer arietinum* L.)
Lintels (*Lens*), (*Lens culinaris* Medik.)
Lupines (*Lupinus* L.)
Vetches (*Vicia* L.)
    Field bean, broad bean, English bean (*Vicia faba* L.)
Sweet peas (*Lathyrus* L.)
    Grass pea (*Lathyrus sativus* L.)
    Earthnut pea (*Lathyrus tuberosus* L.)
*Vigna*
    Mat bean, Turkish gram (*Vigna aconitifolia* (Jacq.) Maréchal)
    Adzuki bean (*Vigna angularis* (Willd.) Ohwi & H. Ohashi)
    Black lentil, black gram (*Vigna mungo* (L.) Hepper)
    Mung bean (*Vigna radiata* (L.) R. Wilczek), "bean sprouts"
    Bambara groundnut (*Vigna subterrane* (L.) Verdc.)
    Rice bean (*Vigna umbellata* (Thunb.) Ohwi & H. Ohashi)
    Zombi pea (*Vigna vexillata* (L.) A. Rich.) (no German name)
    Cowpea (*Vigna unguiculata* (L.) Walp.), in the three subspecies:
        Asparagus bean (*Vigna unguiculata* subsp. *sesquipedalis*)
        Cowpea (*Vigna unguiculata* subsp. *unguiculata*)
        Catjang bean (*Vigna unguiculata* subsp. *cylindrica*)
Tropical green pea (*Cajanus cajan* (L.) Millsp.)
*Macrotyloma*
    Groundnut (*Macrotyloma geocarpum* (Harms) Maréchal & Baudet)
    Horse gram (*Macrotyloma uniflorum* (Lam.) Verdc.)
Goa bean (*Psophocarpus tetragonolobus* (L.) DC.)
African yam bean (*Sphenostylis stenocarpa* (Hochst. ex A. Rich.) Harms)
Hyacinth bean, bonavist bean, *lablab* bean (*Lablab purpureus* (L.) Sweet)
Guar bean, locust bean, carob bean (*Cyamopsis tetragonolobus* (L.) Taub.)
*Canavalia*
    Jack bean (*Canavalia ensiformis* (L.) DC.)
    Sword bean (*Canavalia gladiata* (Jacq.) DC.).
Of the other vegetables, the following are to be understood according to the invention, for example: turtleweed (*Batis* L.), Chinese water chestnut (*Eleocharis dulcis*), marsh mallow (*Althaea officinalis* L.), fennel (*Foeniculum vulgare* (L.) Mill.), garden *asparagus* (*Asparagus officinalis* L.), common rhubarb (*Rheum rhabarbarum*), Japanese rhubarb (*Fallopia japonica* (Houtt.) Ronse Decr.), coriander (*Coriandrum sativum* L.), sweet potato (*Ipomoea batatas* L.), *quinoa* (*Chenopodium quinoa* Willd.), Swedish rapeseed (*Brassica napus*), water *mimosa* (*Neptunia oleracea* Lour.), maniok, mandioca, cassava, cassava or *yucca* in Latin America (*Manihot esculenta* Crantz), New Zealand yam or oca (*Oxalis tuberosa*), olluco, melloco or ullucus (*Ullucus tuberosus*), mashua, also tuberous nasturtium (*Tropaeolum tuberosum*), yacon root (*Smallanthus sonchifolius*), Jerusalem artichoke (*Helianthus tuberosus*) and sunflower (*Helianthus annuus*).

In an additional and/or alternative embodiment, the cereal seed is selected from the group consisting of seeds from wheat (*Triticum* spec.), rye (*Secale* spec.), barley (*Hordeum* spec.), triticale, oats (*Avena* spec.), maize (*Zea mays*), rice (*Oryza* spec.), triticale and millet (*Sorghum* spec., *Panicum* spec., *Pennisetum* spec. and others). Wheat also includes one-grained wheat or small spelt (*T. monococcum*), amelcorn (*T. dicoccum*), hard wheat (*T. durum*), kamut (*T. durum×polonicum*), spelt (*T. spelta*) and soft wheat (*T. aestivum*). Furthermore, millet also includes broomtail millet or common millet (*Panicum miliaceum*), Chinese millet (*Setaria Italica*), sorghum (*Sorghum bicolor* and others), pearl millet (*Pennisetum glaucum*), finger millet or crabgrass (*Eleusine coracana*), teff or annual bunchgrass (*Eragrostis tef*) and fonio (*Digitaria exilis*).

The group of nuts includes nuts in the botanical sense, such as beechnut, hazelnut, walnut (*Juglans regia*), Spanish chestnut (Maroni), acorn, hemp seed, macadamia nut, sycamore nut, tagua nut or water chestnut. These also include the so-called aggregate fruits such as strawberry. However, this group also includes nuts that are not nuts in the botanical sense. These include, for example, the cashew nut, the tigernuts or peanuts (*Arachis hypogaea*), coconut, almond, nutmeg, Brazil nut, pecan nut, pistachio or sheanut.

Of the stone fruit, only the inner pericarp is lignified. The stone fruit include, for example, mango, Mirabelle plum, nectarine, peach, plum, apricot, olive, sour cherry, sweet cherry.

Aggregations of drupes=raspberry, blackberry.

The berries include bananas, citrus fruit, dates, melons, kiwis papayas, and the nightshade family, such as peppers, tomatoes, tamarillo, horseapple, eggplant.

In the sense of the present invention, the amaranth family includes, for example, the sugar beet (*Beta vulgaris vulgaris*), spinach, forage beet, chard and *quinoa*.

The advantages of the method according to the invention include the fact that it is not necessary to use any ionizing radiation, which is harmful to health and might damage the seeds, for non-destructive analysis of seed grains. This method permits a classification of seeds with a high precision. Furthermore, the method is fast and can be automated, so that it can be used not only in process control but also in the actual process of classification and sorting of the seed. The present invention therefore also includes the method for classification and/or sorting of seeds, in which the classification and/or sorting is/are performed automatically.

With the second aspect of the invention, it also extends to the use of terahertz time-domain spectroscopy for classifying and/or sorting of seed, especially for classifying and/or sorting of the listed in connection with the method according to the first aspect of the invention the seed.

Designs and embodiments of the present invention are described in an exemplary form with respect to the accompanying figures, in which:

FIG. 1: shows time-domain spectra of sugar beet seeds. This figure shows the average spectra of the respective classes.

Figure 2:
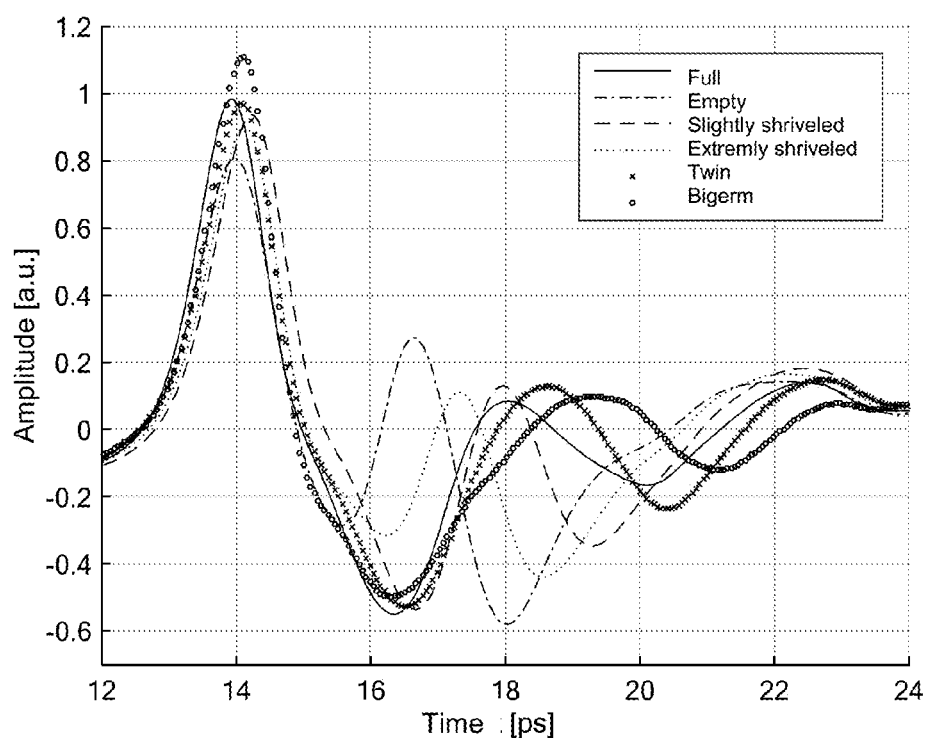

FIG. 2: shows time domain spectra of sugar beet seeds. Detail of FIG. 1 in the range of 12-24 ps. This figure shows the average spectra of the respective classes.

Figure 3:
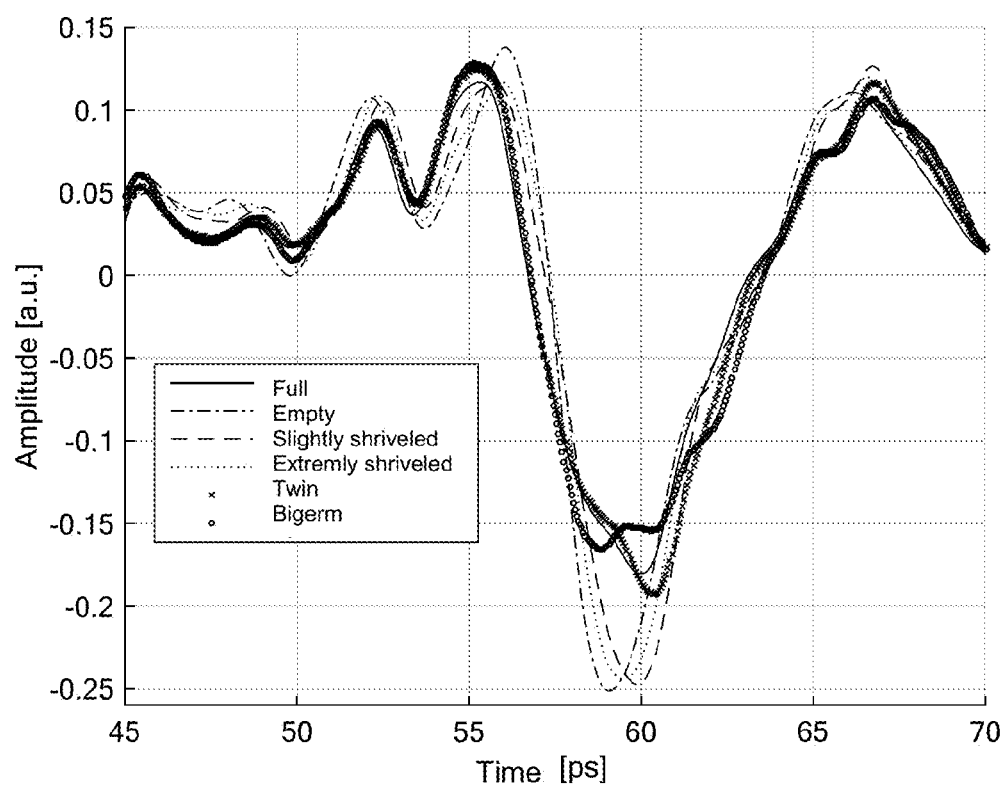

FIG. 3: shows time domain spectra of sugar beet seeds. Detail of FIG. 1 in the range of 45-70 ps. This figure shows the average spectra of the respective classes.

Figure 4:
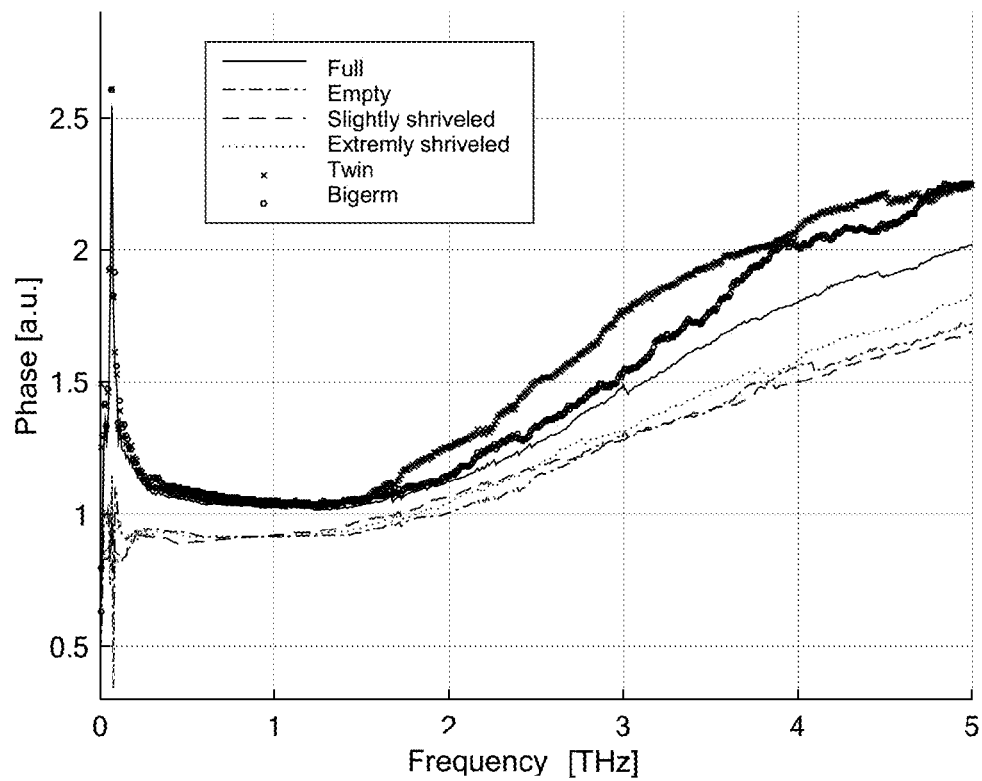

FIG. 4: shows phase spectra of sugar beet seeds. This figure shows the average spectra of the respective classes.

Figure 5:
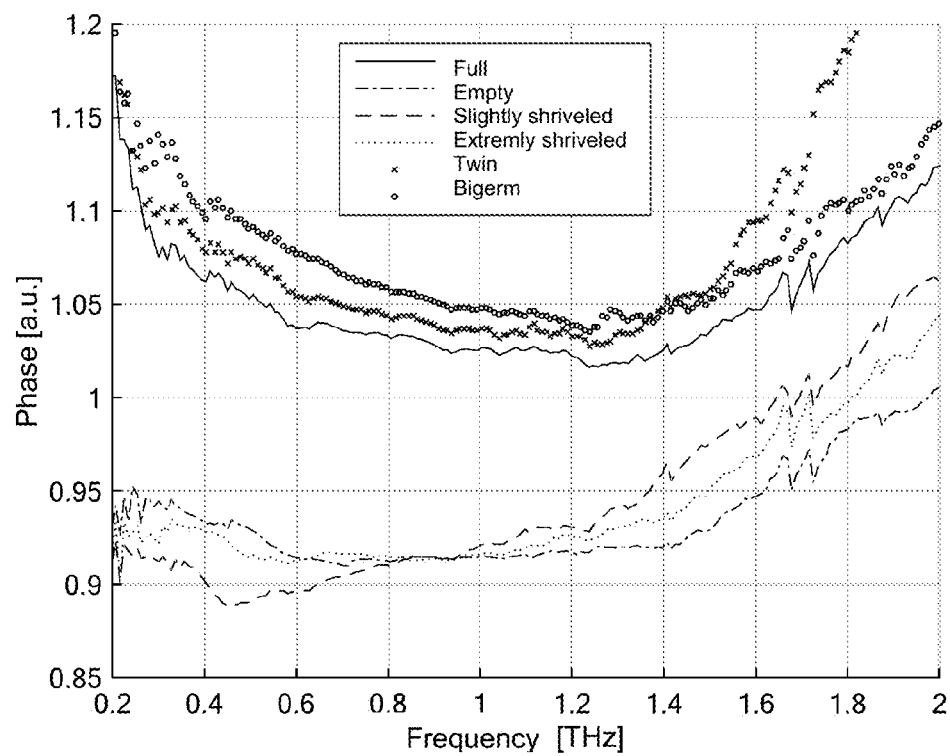

FIG. 5: shows phase spectra of sugar beet seeds. Detail of FIG. 4 in the range of 0.2-2 THz. This figure shows the average spectra of the respective classes.

Figure 6:
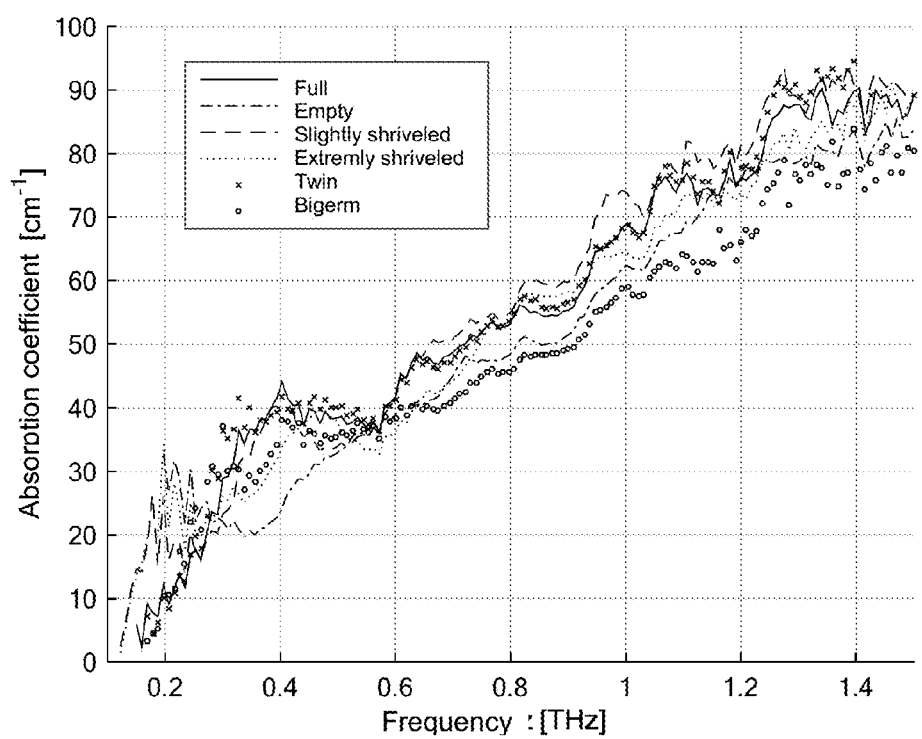

FIG. 6: shows absorption coefficient spectra of sugar beet seeds. This figure shows the average spectra of the respective classes.

Figure 7:
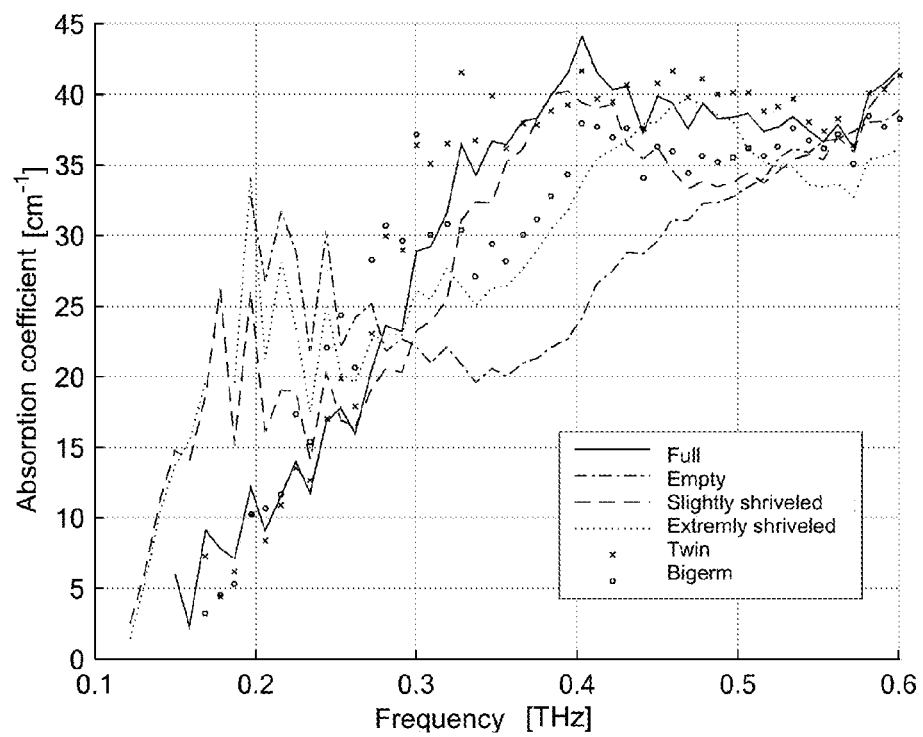

FIG. 7: shows absorption coefficient spectra of sugar beet seeds. Detail of FIG. 6 in the range of 0.1-0.6 THz. This figure shows the average spectra of the respective classes.

Figure 8:
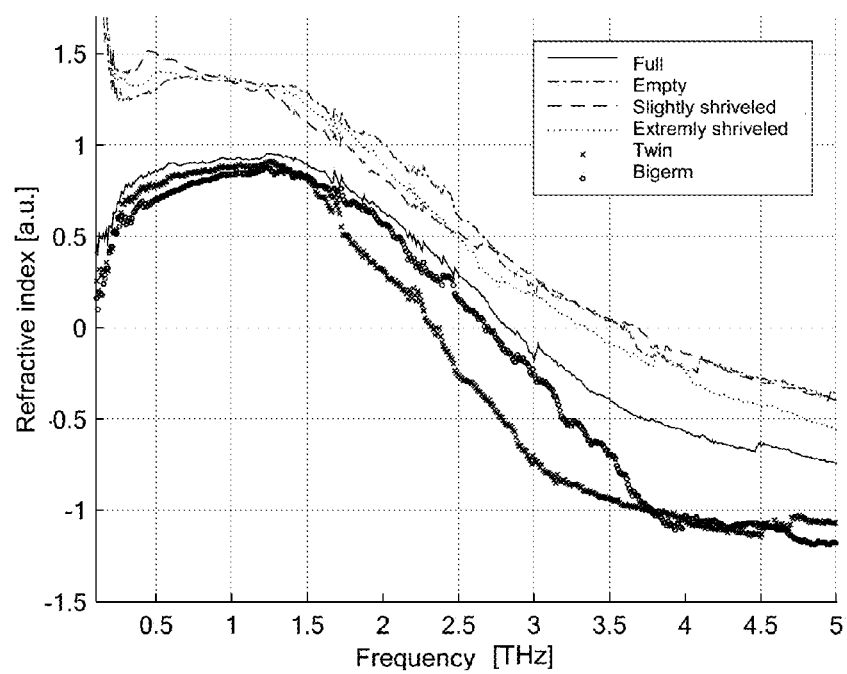

FIG. 8: shows refractive index spectra of sugar beet seeds. This figure shows the average spectra of the respective classes.

Figure 9:
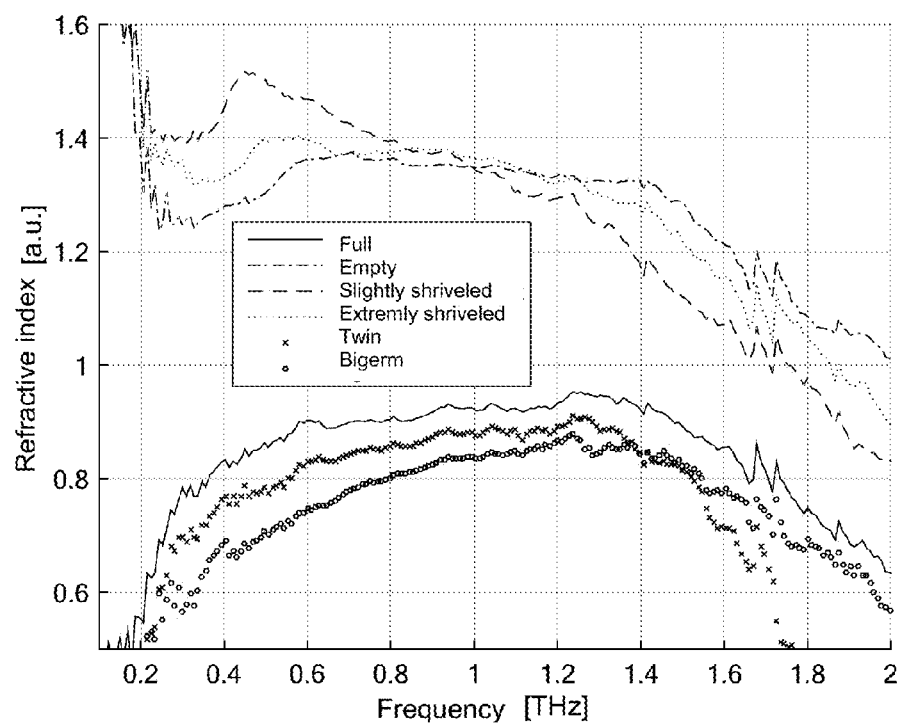

FIG. 9: shows refractive index spectra of sugar beet seeds. Detail of FIG. 8 in the range of 0.1-2 THz. This figure shows the average spectra of the respective classes.

Figure 10:
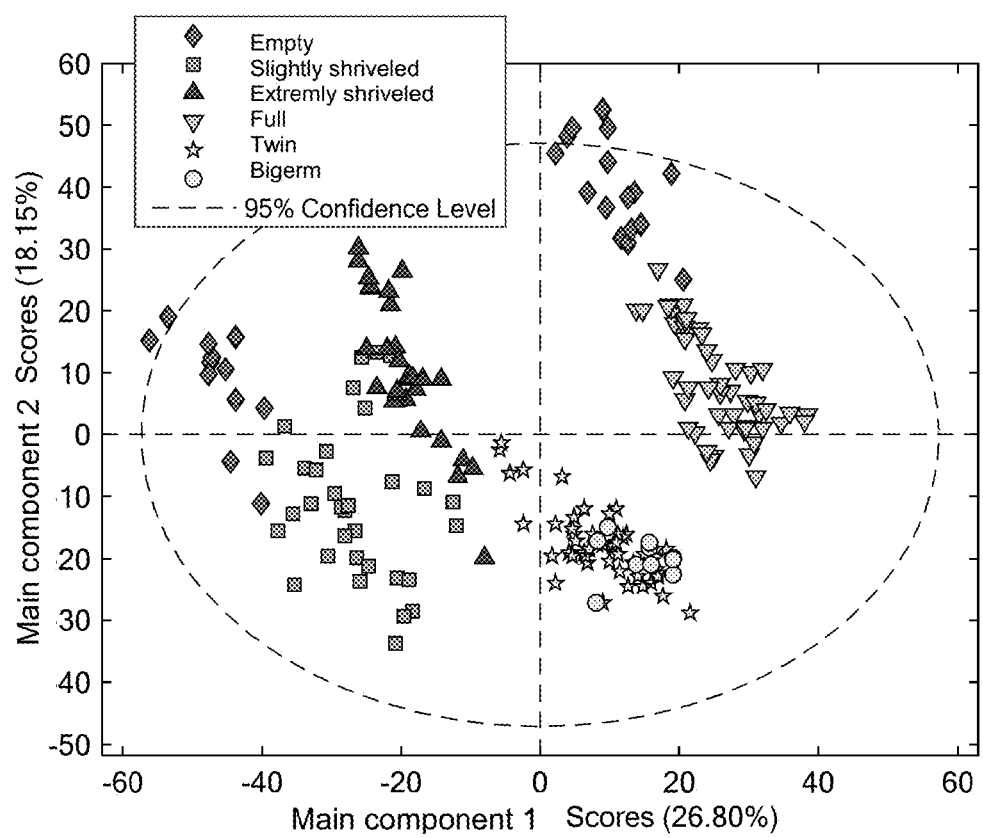

FIG. 10: main component analysis of sugar beet seeds: score diagram of the main components 1 and 2.

Figure 11:
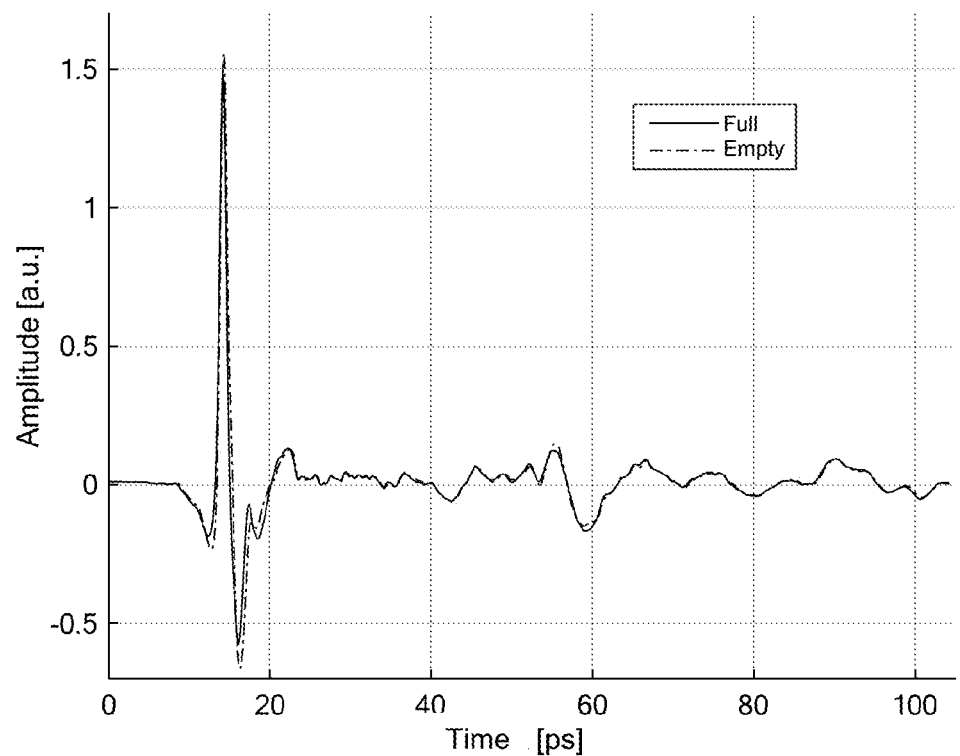

FIG. 11: shows time-domain spectra of onion seeds. This figure shows the average spectra of the two classes.

Figure 12:
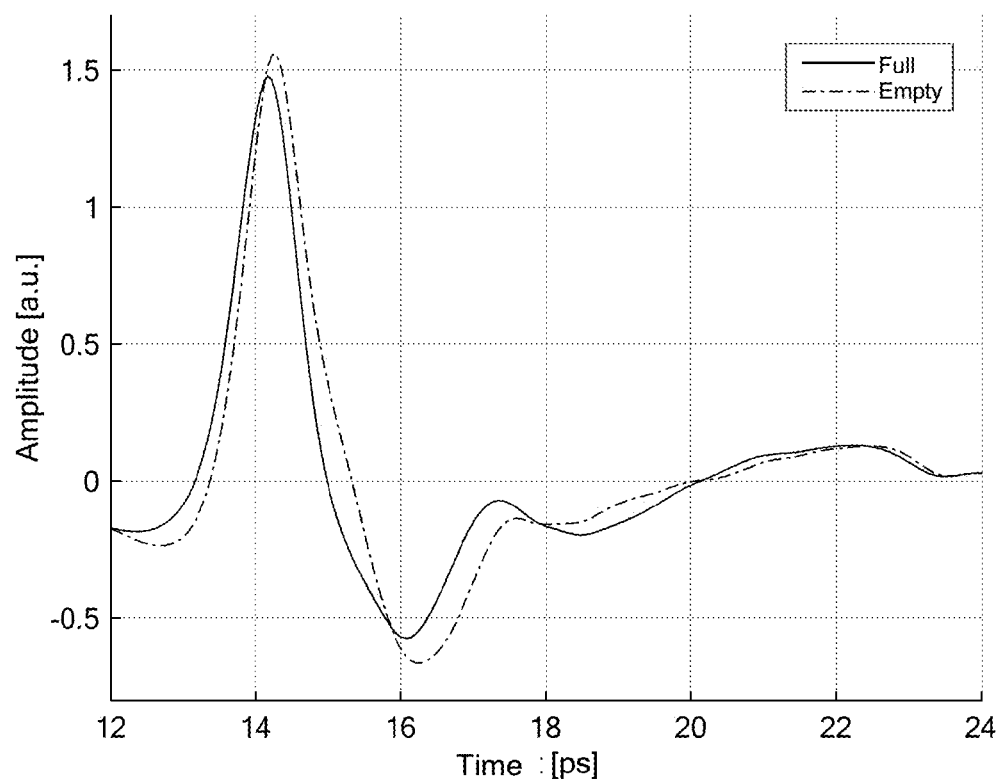

FIG. 12: shows time-domain spectra of onion seeds. Detail of FIG. 11 in the range of 12-24 ps. This figure shows the average spectra of the two classes.

Figure 13:
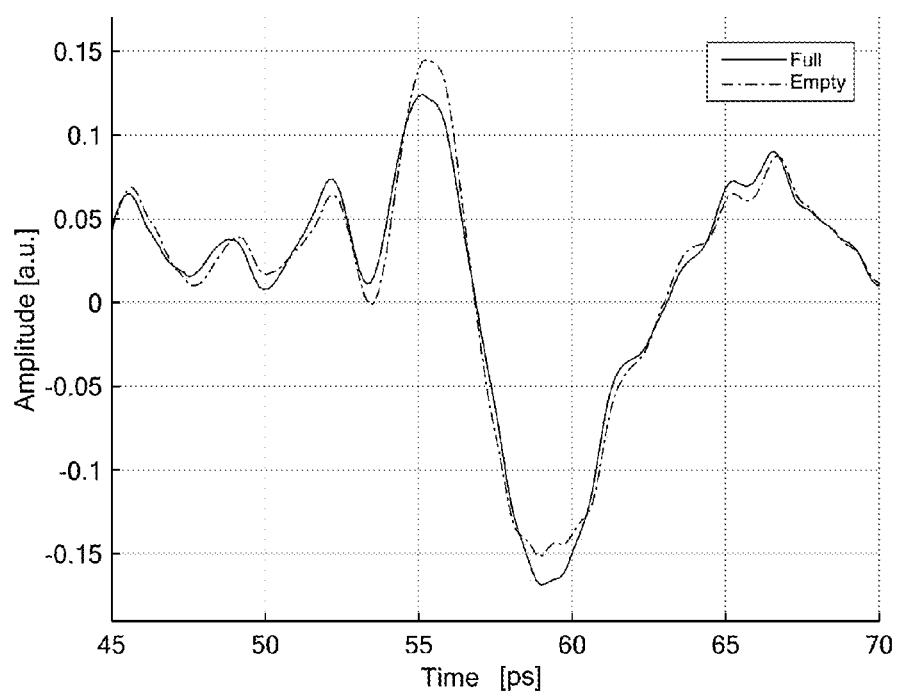

FIG. 13: shows time-domain spectra of onion seeds. Detail of FIG. 11 in the range of 45-70 ps. This figure shows the average spectra of the two classes.

Figure 14:
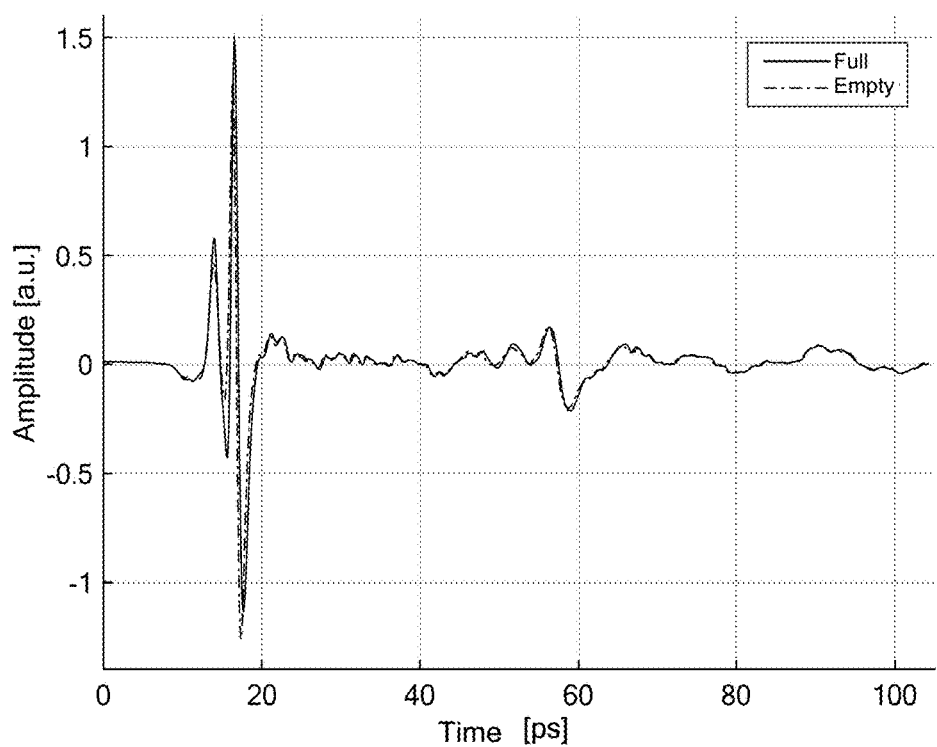

FIG. 14: shows time-domain spectra of pepper seeds. This figure shows the average spectra of the two classes.

Figure 15:
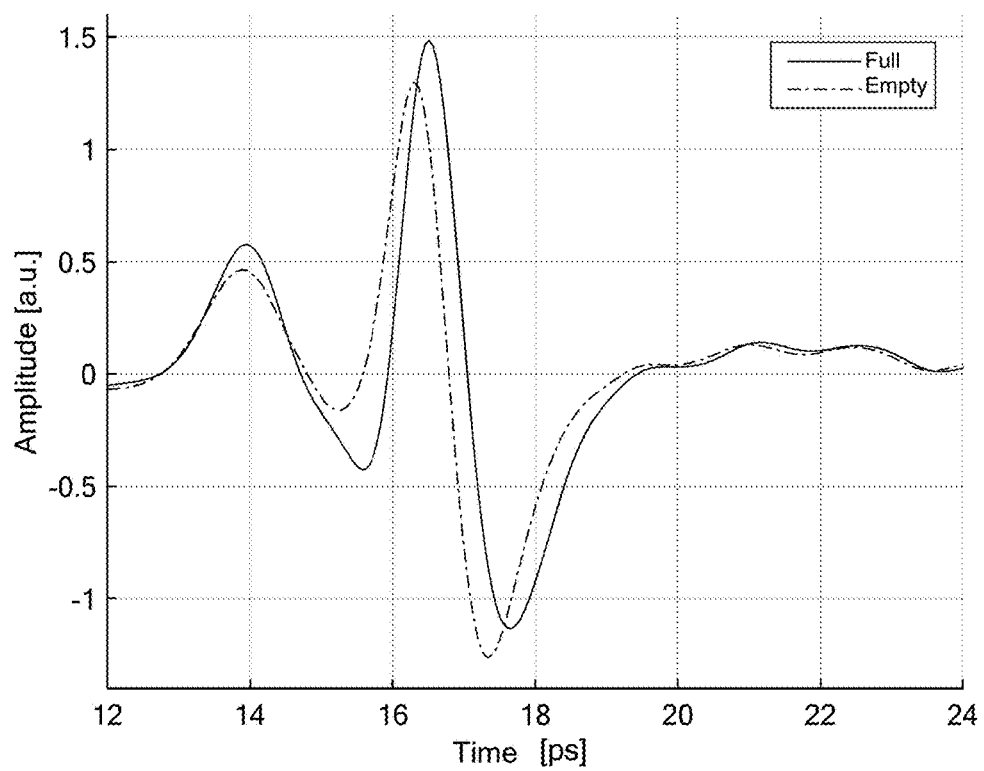

FIG. 15: shows time-domain spectra of pepper seeds. Detail of FIG. 14 in the range of 12-24 ps. This figure shows the average spectra of the two classes.

Figure 16:
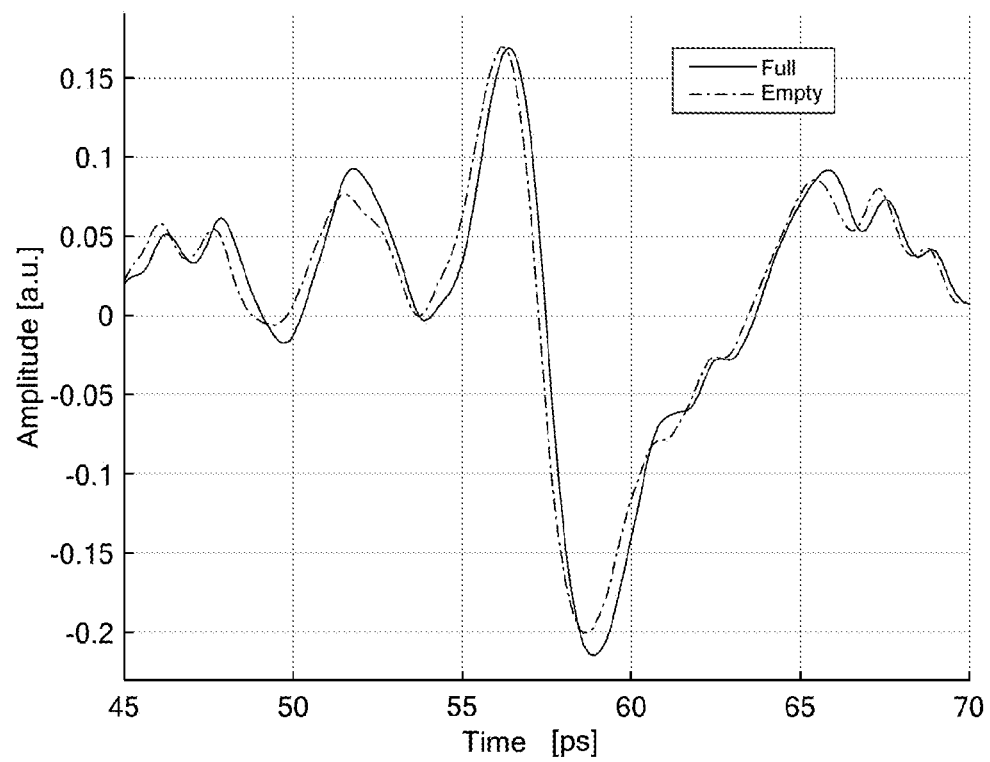

FIG. 16: shows time-domain spectra of pepper seeds. Detail of FIG. 14 in the range of 45-70 ps. This figure shows the average spectra of the two classes.

Figure 17:
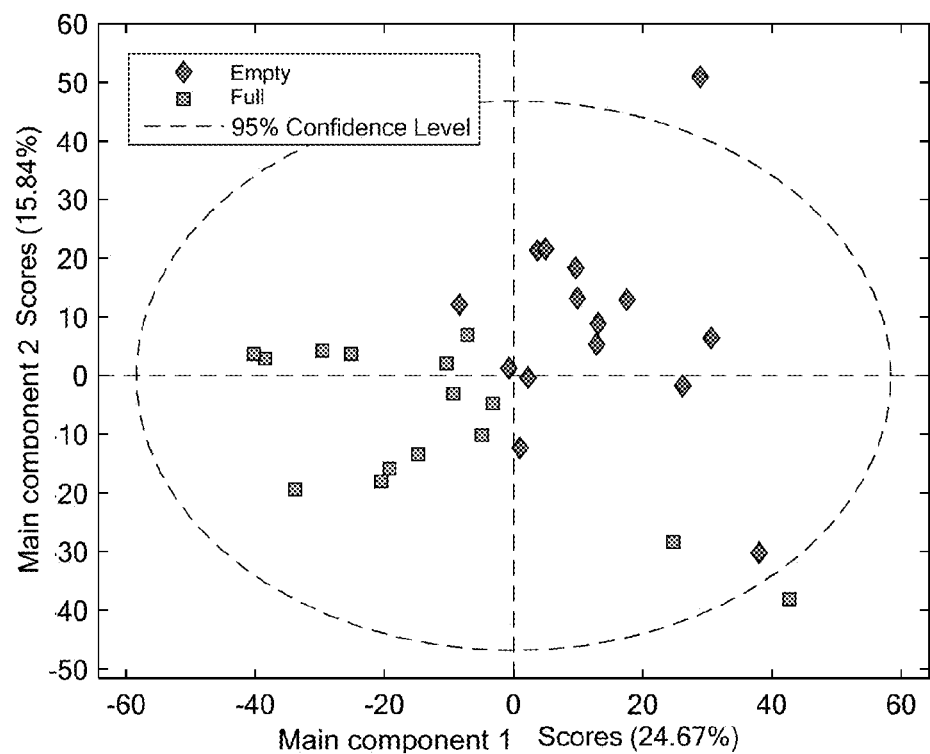

FIG. 17: shows the main component analysis of onion seeds: score diagram of main components 1 and 2.

Figure 18:
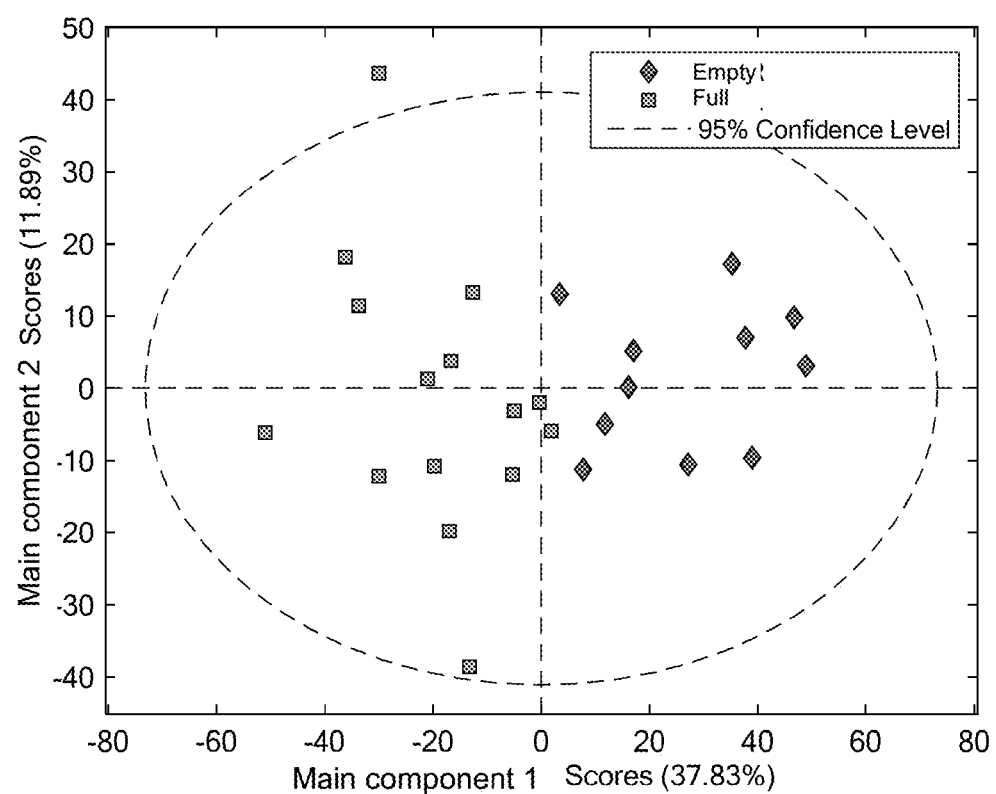

FIG. 18: shows the main component analysis of pepper seeds: score diagram of main components 1 and 2.

Figure 19:
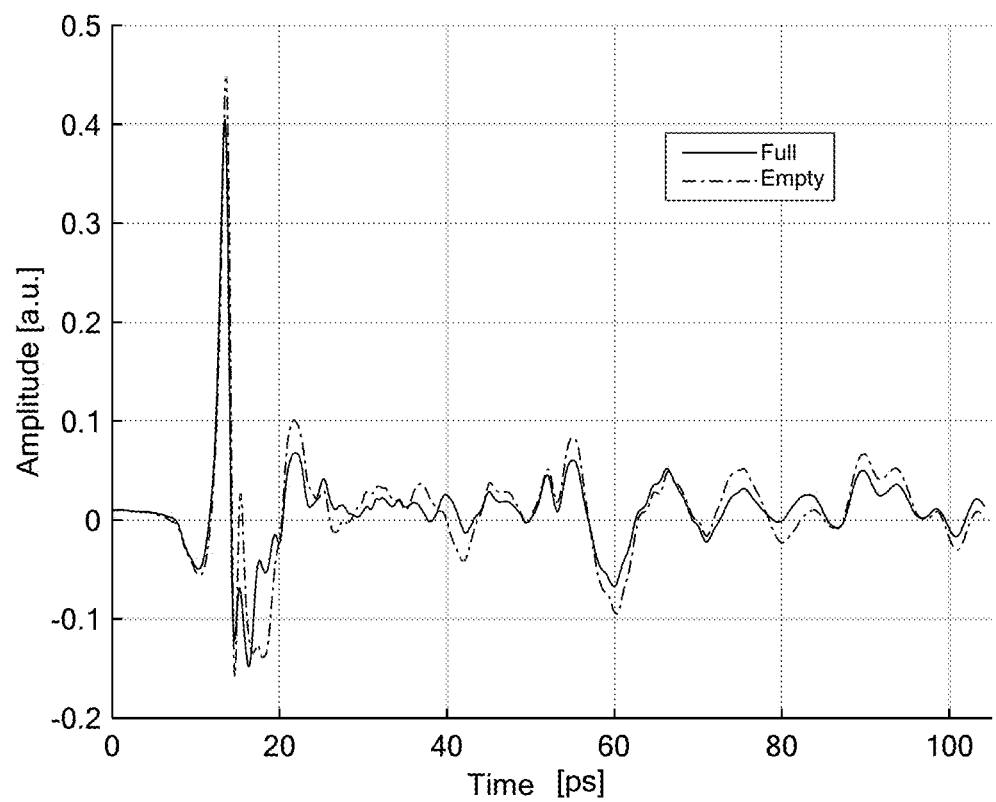

FIG. 19: shows the time-domain spectra of sunflower seeds. This figure shows the average spectra of the two classes.

Figure 20:
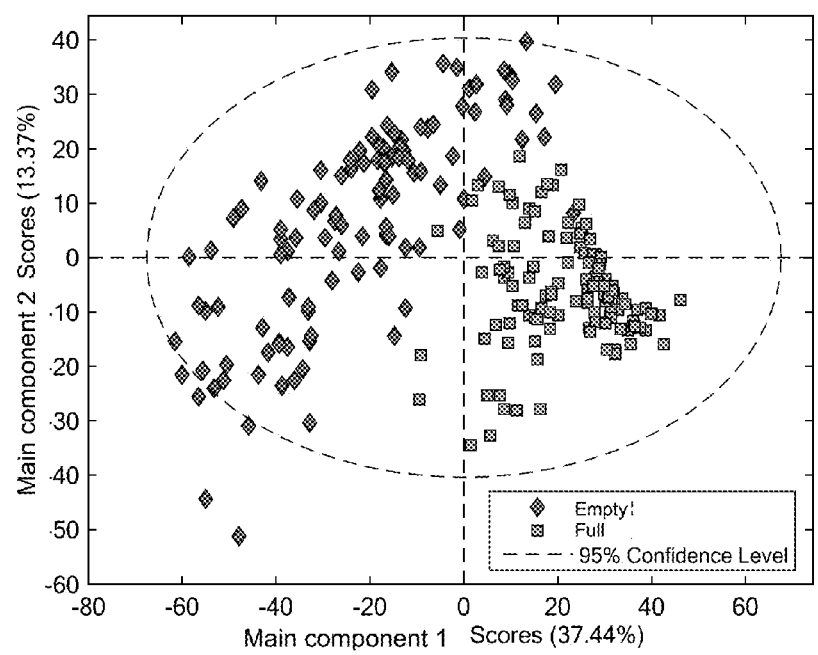

FIG. 20: shows the main component analysis of sunflower seeds: score diagram of main components 1 and 2.

SEED SAMPLES

The quality of the seed classification and sorting method according to the invention is demonstrated below on seeds of various types of crops, such as sugar beet (*B. vulgaris*), onion (*A. cepa*), pepper (*Capsicum*) and sunflower (*H. annuus*). The evaluation of the suitability of the method according to the invention is based on an X-ray diagnostic procedure performed previously in the laboratory to classify the seeds. The classification achieved based on the X-ray diagnostic procedure is referred to below as the "actual class."

Sugar Beets:

The seeds of the sugar beet are divided into 6 calibers based on the grain geometry and grain density. The seed grains of each caliber are subjected to X-ray diagnostics classifying the individual seed grains into the classes 1 through 6 described above. Class 1 is referred to below as "empty," class 2 as "full," class 3 as "slightly shrunken," class 4 as "severely shrunken," class 5 as "twin" and class 6 as "bigerm."

Onions and Peppers:

Seeds of the onion and pepper varieties are divided into two calibers based on the grain geometry and grain density for each variety. The seed grains are also subjected to an X-ray diagnostic procedure. In the case of onion and pepper it is advisable to classify the seeds into the classes "full" and "shrunken," where the class "shrunken" could contain grains of the classes "empty," "slightly shrunken" and "severely shrunken."

Sunflower:

In contrast with the two varieties of vegetables described above, with sunflowers there is no classification of the seeds in calibers. The seed grains were also subjected to the X-ray diagnostic procedure. As was the case with onion and pepper, it is advisable in the case of sunflower to classify the seeds in the classes "full" and "shrunken" or "shriveled."

Specifications for the Terahertz Spectrometer:

The measurements were performed with the "TERA K15" terahertz time-domain spectrometer from Menlo Systems GmbH, Martinsried, Germany. The "TERA K15" spectrometer consists of a laser source with fiber optics, a delay zone with a scanning range of 0-300 ps, a TERA15-TX-FC terahertz emitter antenna and a TERA15-RX-FC terahertz receiver antenna fitting with the former, terahertz-capable optics, a lock-in TERA-C amplifier and a computer with a measurement program for data acquisition and analysis.

The spectrometer offers a dynamic range of >70 dB and a spectral range of >3.5 THz. The built-in femtosecond laser is linearly polarized, emits at 1560 nm with a repeat frequency of 100 MHz with an average laser output power of >60 mW. The pulse length after 2.5 m fiber optics is <90 fs.

To measure the seed grains of all varieties of vegetables, the following measurement settings and parameters are selected: a spectral measurement range of 0.01-10 THz and a delay of 0-104 ps with an interval of 0.05 ps. The integration time pro delay position is 30 msec, which yields a total measurement time of approx. 1 minute per seed grain.

Performing the Terahertz Measurements:

For the measurement, a seed grain as described above is placed in the focal point of the terahertz beam. A terahertz pulse is then applied to the seed grain. The terahertz pulse is generated by the transmitter antenna, passes through the lens, is focused and interacts with the seed grain. The detector antenna records the signal generated by the terahertz pulse after transmission and/or reflection by the seed grain. Multiple terahertz pulses are typically are applied to the seed grain, even with different delay times. The signal of the detector antenna is read out by a computer using a measurement program and the transmission-determined and/or reflection-determined amplitude, the time delay, the phase and/or the spectrum of the signal is/are determined. In additional steps the absorption coefficient and the refractive index of the seed grain can be calculated.

Evaluation and Results

In the following embodiment the method for classification is carried out using terahertz radiation on the basis of a caliber.

Sugar Beets:

FIGS. 1-3 shows the time-domain spectra of the seed of an exemplary caliber (3.16-3.50 mm), where an average spectrum has been formed for each class. FIG. 1 shows the complete spectrum, but FIGS. 2 and 3 show details to illustrate differences in the spectra. The spectra of the six classes show definite differences, for example in the range of 15-22 ps.

Furthermore the spectra of the phase, the absorption coefficient and the refractive index also disclosed differences in a comparison of the classes within a caliber, as shown in FIGS. 4-9. FIGS. 4, 6 and 8 each show the complete spectrum and FIGS. 5, 7 and 9 each show an enlarged detail of the phase, the absorption coefficient and the refractive index.

The information on the time domains, the phase, the absorption coefficient and the refractive index and/or combinations thereof can be used for the classification. In the embodiment in the present case, for example, only the time-domain spectrum is used for classification; the situation is similar with the other types of fruit listed below.

To illustrate the differences in the time-domain spectra and to further investigate the data, the analysis is calculated by performing a main component analysis (PLS Toolbox Version 7.9.1, Eigenvector Research, Inc., Wenatchee, United States of America based on Matlab® 2014b, The MathWorks GmbH, Ismaning, Germany). FIG. 10 shows the score diagram of the main components 1 and 2. The classes "empty," "slightly shrunken," "greatly shrunken," "twin" and "bigerm" occupy the main component space in quadrants II, III and IV and are thus clearly differentiated from the classes "full" and another group of the class "empty" in quadrant I. The boundary between the classes "full" and "empty" in quadrant I is not sharp, i.e., some samples of these two classes may overlap.

To emphasize the differences in the data, the raw data is optimized for further processing for example by means of Savitzky-Golay [method] (A. Savitzky; M. J. E. Golay (1964). "Smoothing and Differentiation of Data by Simplified Least Squares Procedures"; Analytical Chemistry 36 (8): 1627-1639) or moving average smoothing filter (The Scientist and Engineer's Guide to Digital Signal Processing, Chapter 15—Moving Average Filters, by Steven W. Smith, Nov. 17, 2001), wherein the smoothing can also be supplemented with a derivation. In the second step of data processing the entire data set is split into two independent data sets by means of the Kennard-Stone algorithm (R. W. Kennard, R. W. and L. A. Stone (1969) Computer aided design of experiments. Technometrics 11(1), 137-148) (also PLS Toolbox Version 7.9.1, Eigenvector Research, Inc. Wenatchee, United States of America based on Matlab® 2014b, The MathWorks GmbH, Ismaning, Germany). The data selected using the Kennard-Stone algorithm is then used to create the classification model and the remaining data is validated with this data set.

Various algorithms such as the "k-nearest neighbor algorithm" (abbreviated KNN) can be used for the classification (N. S. Altman (1992), "An introduction to kernel and nearest-neighbor nonparametric regression," The American Statistician 46 (3): 175-185. doi:10.1080/00031305.1992. Ser. No. 10/475,879)) or the support vector machine (abbreviated SVM) (N. Cristianini and J. Shawe-Taylor (2000), An Introduction to Support Vector Machines and Other Kernel-Based Learning Methods, First Edition (Cambridge: Cambridge University Press)) may be used for the classification.

The evaluation of the classification is assessed by means of the following quality factors: true positive, true negative, false positive and true positive. Since, as described above, the separation of the class "full" from the remaining classes is of primary concern, then the quality factors are defined as follows: in the case of true positive, seed assigned to the actual class "full" is correctly assigned to the class "full"; in the case of a true negative, seed of another actual class is correctly not assigned to the "full" class; in the case of a false negative, seed from the actual "full" class is falsely assigned to another class; and with a false positive seed from another actual class is falsely assigned to the "full" class.

Table 1 shows the classification of the seed grains from the validation data set. The classification achieves quality factors of 100% with a true positive result, 100% with a true negative, 0% with a false positive and 0% with a false negative, based on the "full" class. If all the classes are included, then 89% of all grains are classified correctly. This result shows that sugar beet seed grains within one caliber can be classified according to the present invention with a high quality.

TABLE 1

Result of the classification of sugar beet seeds by the method according to the invention (=predicted class).

| | | Actual class | | | | | |
| | | empty | slightly shrunken | greatly shrunken s | full | twin | bigerm |
| --- | --- | --- | --- | --- | --- | --- | --- |
| Predicted class | Total | 4 | 11 | 10 | 32 | 37 | 6 |
| | empty | 4 | 0 | 0 | 0 | 0 | 0 |
| | slightly shrunken | 0 | 9 | 3 | 0 | 0 | 0 |
| | greatly shrunken | 0 | 1 | 7 | 0 | 0 | 0 |
| | full | 0 | 0 | 0 | 32 | 0 | 0 |
| | twin | 0 | 1 | 0 | 0 | 37 | 3 |
| | bigerm | 0 | 0 | 0 | 0 | 0 | 3 |

Onion and Pepper:

As already described, only the information about time domains will be discussed here as an example. The time-domain spectra of the onion and pepper seeds, each of an exemplary caliber, are shown in FIGS. 11-16, where an average spectrum has been formed for each class. FIGS. 11 and 14 each show the complete spectrum of the onion seeds and/or pepper seeds. However, FIGS. 12 and 13 for onion seeds and FIGS. 15 and 16 for pepper seeds represent details of the complete spectra illustrating the differences in the spectra.

The data preprocessing and analysis of the onion and pepper seeds were performed as done with the sugar beet. First, a main component analysis was performed, then the data was optimized using a smoothing filter and possibly a derivation as also described above and the respective data set was divided into two independent data sets by means of the Kennard-Stone algorithm. However the main component analysis of the pepper seeds was not calculated with the raw data but instead was calculated with the data that had already been optimized.

The diagram for the score of the main component analysis of the onion seeds is shown in FIG. 17. There is a recognizable separation between the two classed "full" and "shrunken" but the data points for the two groups are situated close together. The situation looks similar in the main component analysis of pepper, represented in FIG. 18. Here again, there is a recognizable differentiation in the two classes "full" and "shrunken" but the two groups of data points are also close together.

The fact that the signal differences in between the onion and pepper seeds turn out smaller than those with the sugar beets can probably be attributed to the size/geometry of the seeds and their embryos. Onion seeds are much smaller than the sugar beet seeds, while the pepper seeds are definitely flatter.

A classification of the seeds of onions and peppers is possible by means of the method according to the invention. Table 2 shows the classification of the validation data set of onion seeds. The quality of the classification is 87.5% true positive, 12.5% false negative, 14.3% false positive and 85.7% true negative. On the whole, 86.7% of the onion seed grains are classified correctly. The classification of the validation data set of the pepper seeds is shown in table 3. All the seed grains were classified correctly, with 100% true positive quality factors, 0% false negative, 0% false positive and 100% true negative. On the whole 100% of the pepper seed grains were classified correctly.

TABLE 2

Results of classification of onion seeds by the method according to the invention (=predicted class).

|  |  | Actual class | |
| --- | --- | --- | --- |
|  |  | shrunken | full |
|  | total | 7 | 8 |
| Predicted | shrunken | 6 | 1 |
| class | full | 1 | 7 |

TABLE 3

Results of classification of pepper seeds with the method according to the invention (=predicted class).

|  |  | Actual class | |
| --- | --- | --- | --- |
|  |  | shrunken | full |
|  | total | 5 | 8 |
| Predicted | shrunken | 5 | 0 |
| class | full | 0 | 8 |

Sunflower:

The time domain spectra of the sunflower seeds are shown in FIG. 19. Since the seeds were not subdivided according to caliber in the case of the sunflower seeds, FIG. 19 shows the average spectra of the two classes.

The data preprocessing and analysis were performed in the same way as for the sugar beet, pepper and onion seeds. However, the main component analysis of the sunflower seeds was not calculated using the raw data but instead using the data that had already been optimized. FIG. 20 shows the score diagram of both main components 1 and 2. Here again, we see fundamentally a separation in the two classed "full" and "empty" but the adjacent data points overlap.

The classification of the validation data set of the sunflower seeds is shown in table 4. The quality of the classification is 98.9% true positive, 1.1% false negative, 0% false positive and 100% true negative. A total of 99.1% of the sunflower seed grains were classified correctly.

TABLE 4

Results of the classification of sunflower seeds with the method according to the invention (=predicted class).

|  |  | Actual class | |
| --- | --- | --- | --- |
|  |  | shrunken | full |
|  | total | 23 | 91 |
| Predicted | shrunken | 23 | 1 |
| class | full | 0 | 90 |

These results show that the method can be used not only for sugar beet seeds but also for seeds from other types of fruits, such as those shown here. In addition, it has been shown that depending on the properties of the grains, a classification without a prior division according to caliber is also possible.

The invention claimed is:

1. A method for classifying seeds by using radiation in the terahertz range, comprises:
    (a) applying an input terahertz pulse to the seed;
    (b) measuring a signal generated by the input terahertz pulse after transmission and/or reflection by the seed;
    (c) comparing the measured signal with the input terahertz pulse to determine a difference;
    (d) determining one or more of the parameters based on the difference between the measured signal and the input terahertz pulse, the parameters being selected from the group consisting of a change in amplitude, a time delay in passing through the seed, additional echo pulses as a result of reflections within the seed, and field oscillations following the input terahertz pulse;
    (e) assigning the seed to a predetermined seed class based on the one or more parameters obtained in step (d) as compared to a corresponding reference value.

2. The method according to claim 1, wherein the method has a sorting accuracy of at least 75%.

3. The method according to claim 1, wherein the method is automated.

4. The method according to claim 1, wherein the terahertz pulse has a duration in the range of 3 picoseconds (ps) to 25 ps.

5. The method according to claim 1, wherein the terahertz pulse has a delay of 0-104 ps with an interval of 0.05 ps.

6. The method according to claim 1, wherein the seed is assigned to the predetermined class based on a determination of an embryo status of the seed, and wherein the embryo status of the seed is determined based on the one or more parameters determined in step (d).

7. The method according to claim 6, wherein the embryo status of the seed is determined based on the change in amplitude, the time delay in passing through the seed, the additional echo pulses as a result of reflections within the seed, and the field oscillations following the input terahertz pulse.

8. The method according to claim 1, wherein the terahertz radiation of the terahertz pulse has a frequency of 0.1 THz-10 THz.

9. The method according to claim 8, wherein the terahertz radiation of the terahertz pulse has a frequency of 0.1-2 THz.

10. The method according to claim 1, wherein the method involves the use of a terahertz time-domain spectrometer.

11. The method according to claim 10, wherein the seed is sorted according to its predetermined seed class after taking it out of the measurement range of the terahertz time-domain spectrometer.

12. The method according to claim 10, wherein the seed is calibrated prior to classification.

13. The method according to claim 10, wherein the method comprises a step of introducing the seed into the measurement range of the spectrometer prior to step (a) and/or a step of taking the seed out of the measurement range of the spectrometer after step (d) and/or after step (e).

14. The method according to claim 1, wherein the seed is selected from the group consisting of vegetable seeds, cereal seeds, grains of pitted fruit, grains of berries, nuts, and grains of Amaranthaceae family.

15. The method according to claim 14, wherein the seed is the seed of the genus selected from the group consisting of Beta, *Allium, Helianthus*, and *Capsicum*.

16. The method according to claim 15, wherein the seed is from the species selected from the group consisting of *Beta vulgaris, Allium cepa*, and *Helianthus annuus*.

\* \* \* \* \*